United States Patent [19]

Tadayuki et al.

[11] Patent Number: 5,668,086
[45] Date of Patent: Sep. 16, 1997

[54] HERBICIDE COMPOSITION

[75] Inventors: Suzuki Tadayuki; Hasabe Keiko; Kurita Kazuhiko; Hioki Yuichi, all of Wakayama, Japan

[73] Assignee: Kao Corporation, Tokyo, Japan

[21] Appl. No.: 737,337

[22] PCT Filed: Nov. 18, 1994

[86] PCT No.: PCT/JP94/01853

§ 371 Date: Nov. 18, 1996

§ 102(e) Date: Nov. 18, 1996

[87] PCT Pub. No.: WO95/31903

PCT Pub. Date: Nov. 30, 1995

[30] Foreign Application Priority Data

May 20, 1994 [JP] Japan ............................ 6-106391

[51] Int. Cl.$^6$ ................ A01N 43/60; A01N 43/40

[52] U.S. Cl. ................ 504/235; 504/116; 504/250; 71/DIG. 1

[58] Field of Search .................... 504/235, 250, 504/116; 71/DIG. 1

[56] References Cited

U.S. PATENT DOCUMENTS 5,538,937  7/1996  Hasebe et al. ................ 504/116

*Primary Examiner*—Brian M. Burn
*Assistant Examiner*—Brian Bembenick
*Attorney, Agent, or Firm*—Oblon, Spivak, McClelland, Maier & Neustadt, P.C.

[57] ABSTRACT

The present invention relates to a herbicide composition comprising (a) paraquat and/or diquat, (b) an anionic surfactant and (c) a chelating agent, wherein a molar ratio (c)/(a) of the component (c) to the component (a) is 0.1–3. The herbicidal effect is markedly enhanced by the incorporation of the chelating agent.

11 Claims, No Drawings

HERBICIDE COMPOSITION

This application is A 371 of PCT/JP94/01953 filed Nov. 18, 1994.

1. Technical Field

The present invention relates to a herbicide composition, and particularly to a herbicide composition enhanced in its herbicidal effect.

2. Background Art

Paraquat (1,1'-dimethyl-4,4'-bipyridinium dichloride) and diquat (1,1'-ethylene-2,2'-bipyridinium dibromide) are bipyridinium type contact herbicides, have no selectivity and exhibit strong weed-killing power by a foliage treatment. Therefore, they are widely used. In herbicide compositions containing these compounds, in which their herbicidal components are diluted with water before their sprinkling, an anionic surfactant is incorporated for the purpose of evenly applying such a liquid chemical to the surfaces of stems and leaves of a target plant and causing the liquid chemical applied to remain for a long period of time on the stems and leaves so as to penetrate into the plant body (Japanese Patent Application Laid-Open No. 230608/1992).

However, the herbicidal effects of these compositions containing the bipyridinium type herbicide and the anionic surfactant have not been fully satisfactory. On the contrary, the herbicidal effects have been lowered according to the kind of an anionic surfactant to be used. The cause of this reduction in activity is considered to be attributed to the fact that the bipyridinium type herbicide forms a complex with the anionic surfactant.

The above-described bipyridinium type herbicides have also involved a problem that the amount of the herbicide to be used is limited due to their high toxicity.

Accordingly, it is an object of the present invention to provide a composition in which the herbicidal effect of a bipyridinium type herbicide is enhanced.

DISCLOSURE OF THE INVENTION

In view of the foregoing circumstances, the present inventors have added various components to a combined system containing a bipyridinium type herbicide and an anionic surfactant to carry out an investigation as to the effects of such components for enhancing the herbicidal activity. As a result, it has been found that when a chelating agent is added in a proportion of 0.1–3 moles per mole of the pyridinium type herbicide, the herbicidal activity is markedly enhanced, thus leading to completion of the present invention.

According to the present invention, there is thus provided a herbicide composition comprising the following components (a), (b) and (c):

(a) paraquat and/or diquat;

(b) an anionic surfactant; and (c) a chelating agent, wherein a molar ratio (c)/(a) of the component (c) to the component (a) is 0.1–3.

BEST MODE FOR CARRYING OUT THE INVENTION

The component (a) in the present invention is an active component for weeding. Paraquat and diquat can be used either singly or in combination. No particular limitation is imposed on the amount of the component (a) to be incorporated into the composition so far as it is sufficient to attain satisfactory herbicidal activity. It is also permissible to prepare a composition containing the component (a) at a high concentration in advance and dilute the composition at the time of use. Specifically, the component (a) is incorporated so as to give a concentration of preferably 0.1–50 wt. % (hereinafter indicated merely by "%"), more preferably 0.1–20%, particularly preferably 0.5–15% of the total weight of the composition. At the time the herbicide composition is used, it is preferably diluted for use in such a manner that the concentration of the component (a) amounts to 0.005–0.8%, particularly 0.005–0.5%.

Examples of the anionic surfactant of the component (b) include salts of higher fatty acids, alkyl(or alkenyl)sulfates, polyoxyalkylene alkyl(or alkenyl)ether sulfates, polyoxyalkylene alkyl(or alkenyl)aryl ether sulfates, polyoxyalkylene styrylphenyl ether sulfates, mono- or di-alkyl(or alkenyl)benzenesulfonates, alkyl(or alkenyl)naphthalenesulfonates, condensates of an alkyl(or alkenyl)naphthalenesulfonate with formaldehyde, alkyl(or alkenyl)diphenyl ether sulfonates, alkyl(or alkenyl)sulfonates, alkyl(or alkenyl)sulfosuccinates, mono- or di-alkyl(or alkenyl)phosphates, polyoxyalkylene mono- or di-alkyl (or alkenyl) ether phosphates, polyoxyalkylene mono- or di-phenyl ether phosphates, polyoxyalkylene mono- or di-alkyl(or alkenyl)phenyl ether phosphates, salts of polycarboxylic acids, alkyl (or alkenyl)polyoxyalkylene ether acetates and N-methyl-fatty acid taurides. Of these, the alkyl(or alkenyl)sulfates, polyoxyalkylene alkyl(or alkenyl)ether sulfates, polyoxyalkylene alkyl(or alkenyl)aryl ether sulfates, alkyl(or alkenyl)naphthalenesulfonates, mono- or di-alkyl(or alkenyl)benzenesulfonates, polyoxyalkylene mono- or di-alkyl(or alkenyl)ether phosphates, polyoxyalkylene mono- or di-phenyl ether phosphates, polyoxyalkylene mono- or di-alkyl(or alkenyl)phenyl ether phosphates, salts of polycarboxylic acids, salts of saturated or unsaturated higher fatty acids and alkyl(or alkenyl)polyoxyalkylene ether acetates are more preferred. Of these, the alkyl(or alkenyl)sulfates, polyoxyalkylene alkyl(or alkenyl)ether sulfates, polyoxyalkylene alkyl(or alkenyl)ether acetates, polyoxyalkylene mono- or di-alkyl(or alkenyl)ether phosphates, salts of saturated or unsaturated higher fatty acids, alkyl(or alkenyl)benzenesulfonates and alkyl(or alkenyl)naphthalenesulfonates are particularly preferred. Among others, the polyoxyalkylene alkyl(or alkenyl)ether acetates and polyoxyalkylene mono- or di-alkyl(or alkenyl) ether phosphates are most preferred.

Preferred alkyl or alkenyl groups or fatty acid residues of these anionic surfactants are those having 4–26 carbon atoms with those having 8–26 carbon atoms being more preferred. These alkyl or alkenyl groups or fatty acid residues may be either linear or branched. The polyoxyalkylene groups in the above anionic surfactants include polyoxyethylene, polyoxypropylene and polyoxybutylene groups with the polyoxyethylene group being particularly preferred. The number of moles of the polyoxyalkylene group to be added is preferably 1–20, particularly 1–10. Examples of salts of the anionic surfactants include salts with an alkali metal such as sodium or potassium, salts with an alkaline earth metal such as calcium or magnesium, ammonium salts, and salts with an alkanolamine such as mono-, di- or tri-ethanolamine.

Specific preferable examples of the anionic surfactants include $C_{8-24}$-alkylsulfates, polyoxyethylene (EO=1–10) $C_{8-24}$-alkyl ether sulfates, polyoxyethylene (EO=1–10) $C_{8-24}$-alkylphenyl ether sulfates, $C_{8-24}$-alkylbenzenesulfonates, $C_{4-24}$-alkylnaphthalenesulfonates, polyoxyethylene (EO=1–10) mono- or di-$C_{8-24}$-alkyl ether phosphates, salts of saturated or unsaturated $C_{8-24}$-fatty acids and $C_{8-24}$-alkyl(or alkenyl)polyoxyethylene (EO=1–20)ether acetates.

The amount of these anionic surfactants (b) to be incorporated into the herbicide composition according to the present invention is preferably within a range of 0.1–20, particularly 0.3–10 in terms of a weight ratio (b)/(a) of the component (b) to the component (a).

No particular limitation is imposed on the chelating agent (c) useful in the practice of the present invention so far as it has the ability to chelate an metal ion. Examples of the chelating agent (c) used in the present invention include aminopolycarboxylic acid type chelating agents, aromatic or aliphatic carboxylic acid type chelating agents, amino acid type chelating agents, ether polycarboxylic acid type chelating agents, phosphonic acid type chelating agents, hydroxycarboxylic acid type chelating agents, polyelectrolyte type chelating agents (including oligomers) and dimethylglyoxime (DG). These chelating agents may be in the form of either an acid or a salt such as the sodium, potassium or ammonium salt.

Specific examples of the aminopolycarboxylic acid type chelating agents include:

a) compounds represented by a chemical formula $R^1NX_2$;
b) compounds represented by a chemical formula $NX_3$;
c) compounds represented by a chemical formula $R^1-NX-CH_2CH_2-NX-R^1$;
d) compounds represented by a chemical formula $R^1-NX-CH_2CH_2-NX_2$;
e) compounds represented by a chemical formula $X_2N-R^2-NX_2$; and
f) compounds similar to the compounds e), which contain 4 or more Xs, for example, a compound represented by a formula

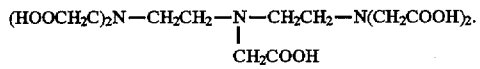

In the above formulae, X denotes —$CH_2COOH$ or —$CH_2CH_2COOH$, $R^1$ means one of groups contained in known chelating agents of this kind, such as a hydrogen atom, alkyl groups, a hydroxyl group and hydroxyalkyl groups, and $R^2$ represents one of groups contained in known chelating agents of this kind, such as alkylene groups and cycloalkylene groups.

Representative examples of the aminopolycarboxylic acid type chelating agents include ethylenediaminetetraacetic acid (EDTA), cyclohexanediaminetetraacetic acid (CDTA), nitrilotriacetic acid (NTA), iminodiacetic acid (IDA), N-(2-hydroxyethyl)iminodiacetic acid (HIMDA), diethylenetriaminepentaacetic acid (DTPA), N-(2-hydroxyethyl) ethylenediaminetriacetic acid (EDTA-OH) and glycol ether diaminetetraacetic acid (GEDTA), and besides salts (for example, the sodium salts and potassium salts) thereof.

Examples of the aromatic or aliphatic carboxylic acid type chelating agents include oxalic acid, succinic acid, pyruvic acid and anthranilic acid, and besides salts (for example, the sodium salts and potassium salts) thereof. Examples of the amino acid type chelating agents used in the present invention include glycine, serine, alanine, lysine, cystine, cysteine, ethionine, tyrosine, methionine, and salts (for example, the sodium salts and potassium salts) and derivatives thereof.

Examples of the ether polycarboxylic acid type chelating agents include compounds represented by the following formula (1), analogous compounds to the compounds represented by the following formula and salts (for example, the sodium salts and potassium salts) thereof:

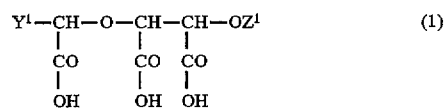

wherein $Y^1$ denotes a hydrogen atom, —$CH_2COOH$ or —COOH, and $Z^1$ means a hydrogen atom,

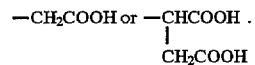

Examples of the phosphonic acid type chelating agents include iminodimethylphosphonic acid (IDP), alkyldiphosphonic acids (ADPAs) and salts (for example, the sodium salts and potassium salts) thereof.

Examples of the hydroxycarboxylic acid type chelating agents include malic acid, citric acid, glycolic acid, heptonic acid, tartaric acid and salts (for example, the sodium salts and potassium salts) thereof.

Examples of the polyelectrolyte type chelating agents (including oligomers) include acrylic acid polymers, maleic anhydride polymers, α-hydroxyacrylic acid polymers, itaconic acid polymers, copolymers composed of at least two of constituent monomers of these polymers, epoxysuccinic acid polymers and salts (for example, the sodium salts and potassium salts) thereof.

Among these chelating agents (c), preferred chelating agents are the aminopolycarboxylic acid type chelating agents, aromatic or aliphatic carboxylic acid type chelating agents, amino acid type chelating agents, ether polycarboxylic acid type chelating agents and hydroxycarboxylic acid type chelating agents. Specific examples thereof include EDTA, CDTA, NTA, HIMDA, DTPA, EDTA-OH, GEDTA, oxalic acid, succinic acid, pyruvic acid, glycine, cysteine, malic acid, citric acid, glycolic acid, heptonic acid, tartaric acid, the ether polycarboxylic acids represented by the formula (1) and salts thereof. Specific examples of particularly preferred chelating agents include DTPA, EDTA, ETA-OH (a compound represented by the formula (1) in which $Y^1$ is $CH_2COOH$, and $Z^1$ is H), cysteine, glycine, gluconic acid and salts (the sodium salts, potassium salts and the like) thereof.

The molar ratio (c)/(a) of the components (c) to the component (a) to be incorporated is preferably 0.1–3, particularly 0.2–2. If the molar ratio is lower than 0.1, the effect of enhancing the herbicidal activity by the component (c) cannot be satisfactorily brought about. Even if the molar ratio exceeds 3, the effect by the incorporation of the component (c) is not markedly improved as compared with the case where the molar ratio is 3.

Into the herbicide composition according to the present invention, other herbicides, bactericides, pesticides and the like may be incorporated within limits not impeding the effects of the present invention. Solvents, pH adjustors, inorganic salts, thickeners, coloring matter, perfume bases and the like may also be added to the herbicide composition according to the present invention as needed.

The herbicide composition according to the present invention can be prepared by a method known per se in the art, for example, by mixing and stirring the individual components. The herbicide composition may be provided in the form of an aqueous solution, a solid such as powder or granules, an aqueous dispersion, or the like. It is preferable to prepare a composition in the form of a solid such as powder or granules, or an aqueous dispersion of high concentration and dilute it with water at the time of use so as to sprinkle the diluted composition where one hopes to weed.

EXAMPLES

The present invention will hereinafter be described in detail by the following Examples. However, this invention is not limited to these examples.

Example 1

(Preparation of herbicide composition)

An anionic surfactant (sodium butylnaphthalenesulfonate or ammonium lauryl sulfate) and ion-exchanged water were used to prepare a 0.01% aqueous solution of the anionic surfactant. To the aqueous solution, a bipyridinium type herbicide (paraquat, or paraquat and diquat) was added to prepare a solution in which 0.01% (100 ppm) of the herbicide was contained as an active ingredient. A chelating agent (tetrasodium ethylenediaminetetraacetate or pentasodium diethylenetriaminepentaacetate) was then added to this solution in a predetermined molar ratio to the herbicide, thereby obtaining a herbicide composition.

(Evaluation method)

Seeds of crab grass are sowed in pots having an inner diameter of 12 cm, into which a soil obtained by mixing fertile soil collected from a paddy field, river sand and a commercially-available compost in a weight ratio of 7:2:1 is placed, to germinate them. In order to enhance uniformity of individuals among the pots, pots in which the growth of crab grass is abnormal are discarded. Pots in which crab grass grew to a plant length of about 18 cm were used in a test. A herbicide composition sample was sprayed on crab grass by means of a spray gun (RG type, manufactured by IWATA AIR COMPRESSOR MFG. CO., LTD) in such a manner that it was evenly applied to the whole of crab grass in the pots in a proportion corresponding to 10 liters/are, thereby evaluating the weed-killing efficacy of the sample.

The evaluation of the weed-killing efficacy was conducted by weighing the fresh weight of an above ground part on the third day after the sprinkling to determine a percent weeding in accordance with the following equation on the basis of the fresh weight of an above ground part in an untreated section. The results are shown in Table 1.

$$\text{Percent weeding} = \frac{(\text{Fresh weight of above ground part in untreated section, g}) - (\text{Fresh weight of above ground part in treated section, g})}{(\text{Fresh weight of above ground part in untreated section, g})} \times 100 \,(\%)$$

TABLE 1

| | | Bipyridinium type herbicide (%) | | Anionic surfactant (%) | | Chelating agent (molar ratio (c)/(a)) | | Percent weeding (%) |
|---|---|---|---|---|---|---|---|---|
| | | Paraquat | Paraquat/diquat (1:1 by wt.) | Sodium butyl-naphthalene-sulfonate | Ammonium lauryl sulfate | Tetrasodium ethylenediamine-tetraacetate | Pentasodium diethylenetriamine-pentaacetate | |
| Inv. prod. | 1 | 0.01 | — | 0.01 | — | 0.5 | — | 86.4 |
| | 2 | 0.01 | — | 0.01 | — | 1.0 | — | 90.2 |
| | 3 | 0.01 | — | 0.01 | — | 2.0 | — | 88.1 |
| Comp. prod. | 1 | 0.01 | — | — | — | — | — | 72.4 |
| | 2 | 0.01 | — | 0.01 | — | — | — | 46.6 |
| | 3 | 0.01 | — | — | — | 0.5 | — | 71.9 |
| Inv. prod. | 4 | 0.01 | — | 0.01 | — | — | 0.5 | 88.6 |
| | 5 | 0.01 | — | 0.01 | — | — | 1.0 | 89.1 |
| | 6 | 0.01 | — | 0.01 | — | — | 2.0 | 91.5 |
| Comp. prod. | 4 | 0.01 | — | — | — | — | — | 72.4 |
| | 5 | 0.01 | — | 0.01 | — | — | — | 46.6 |
| | 6 | 0.01 | — | — | — | — | 0.5 | 70.9 |
| Inv. prod. | 7 | — | 0.01 | — | 0.01 | 0.5 | — | 87.8 |
| | 8 | — | 0.01 | — | 0.01 | 1.0 | — | 92.4 |
| | 9 | — | 0.01 | — | 0.01 | 2.0 | — | 88.0 |
| Comp. prod. | 7 | — | 0.01 | — | — | — | — | 70.8 |
| | 8 | — | 0.01 | 0.01 | — | — | — | 54.1 |
| | 9 | — | 0.01 | — | — | 0.5 | — | 70.5 |

It is understood from Table 1 that when a chelating agent is incorporated into a system in which paraquat and/or diquat and an anionic surfactant are incorporated, the weed-killing effects of paraquat and diquat are enhanced.

Example 2

(Preparation of herbicide composition)

Diluent solutions containing an anionic surfactant and a chelating agent either singly or in combination were prepared with ion-exchanged water so as to give their corresponding predetermined concentrations shown in Table 2. Gramoxone® (containing 30% of paraquat as an active ingredient) and Priglox L® (containing 7% of diquat and 5% of paraquat as active ingredients), which are commercially-available bipyridinium type herbicides, were diluted with the diluent solutions thus obtained in such a manner that the concentrations of the active ingredients in the resulting dilute solutions each amounted to 50 ppm, thereby obtaining respective herbicide compositions.

Besides, Gramoxone® and Priglox L® were separately diluted with ion-exchanged water so as to give an active ingredient concentration of 100 ppm, thereby preparing dilute solutions as comparative examples.

(Evaluation method)

The percent weeding of each test sample was determined in the same manner as in Example 1. The results obtained are shown in Table 2.

TABLE 2

| No. | Bipyridinium type herbicide (a) (concentration of original agricultural chemical) | (ppm) | Anionic surfactant (b) | (ppm) | Chelating agent (c) | (ppm) | (b)/(a) (wt. ratio) | (c)/(a) (molar ratio) | Percent weeding (%) |
|---|---|---|---|---|---|---|---|---|---|
| 1 | Gramoxone ™ | 100 | — | — | — | — | — | — | 67.5 |
| 2 | Gramoxone ™ | 50 | — | — | — | — | — | — | 38.1 |
| 3 | Gramoxone ™ | 50 | — | — | EDTA.2Na | 32.6 | — | 0.5/1 | 40.0 |
| 4 | Gramoxone ™ | 50 | Ammonium POE(4.5) lauryl ether acetate | 100 | — | — | 2/1 | — | 71.3 |
| 5 | Gramoxone ™ | 50 | Ammonium POE(4.5) lauryl ether acetate | 100 | EDTA.2Na | 32.6 | 2/1 | 0.5/1 | 95.1 |
| 6 | Gramoxone ™ | 50 | — | — | Cysteine | 17.6 | — | 0.75/1 | 45.2 |
| 7 | Gramoxone ™ | 50 | Triethanolamine POE(3) lauryl ether sulfate | 50 | — | — | 1/1 | — | 64.6 |
| 8 | Gramoxone ™ | 50 | Triethanolamine POE(3) lauryl ether sulfate | 50 | Cysteine | 17.6 | 1/1 | 0.75/1 | 86.9 |
| 9 | Gramoxone ™ | 50 | — | — | Na gluconate | 84.8 | — | 2/1 | 33.8 |
| 10 | Gramoxone ™ | 50 | POE(3) $C_{12/13}$ ether phosphoric monoester | 200 | — | — | 4/1 | — | 76.3 |
| 11 | Gramoxone ™ | 50 | POE(3) $C_{12/13}$ ether phosphoric monoester | 200 | Na gluconate | 84.8 | 4/1 | 2/1 | 93.5 |
| 12 | Priglox L ™ | 100 | — | — | — | — | — | — | 65.7 |
| 13 | Priglox L ™ | 50 | — | — | — | — | — | — | 35.8 |
| 14 | Priglox L ™ | 50 | — | — | ETA-OH | 14.6 | — | 0.25/1 | 37.1 |
| 15 | Priglox L ™ | 50 | Castor oil fatty acid potash soap | 25 | — | — | 0.5/1 | — | 55.2 |
| 16 | Priglox L ™ | 50 | Castor oil fatty acid potash soap | 25 | ETA-OH | 14.6 | 0.5/1 | 0.25/1 | 88.6 |
| 17 | Priglox L ™ | 50 | — | — | Glycine | 12.4 | — | 1/1 | 35.2 |
| 18 | Priglox L ™ | 50 | Sodium dodecylbenzene-sulfonate | 300 | — | — | 6/1 | — | 68.4 |
| 19 | Priglox L ™ | 50 | Sodium dodecylbenzene-sulfonate | 300 | Glycine | 12.4 | 6/1 | 1/1 | 90.3 |

POE(): POE means abbreviation of polyoxyethylene, and the inside number of a bracket indicates the average mol number of added POE.

As apparent from Table 2, it is understood that when a chelating agent is incorporated into a system in which paraquat and/or diquat and an anionic surfactant are incorporated, the weed-killing effects of paraquat and diquat are enhanced.

INDUSTRIAL APPLICABILITY

According to the present invention, a bipyridinium type herbicide, an anionic surfactant and a chelating agent were blended in a certain ratio, thereby preventing the bipyridinium type herbicide and the anionic surfactant from forming a complex. Therefore, the herbicidal effect of the herbicide is markedly enhanced. As a result, the amount of paraquat and/or diquat to be used can be made less than ever. Their safety for the human body is hence improved. It goes without saying that the compositions according to the present invention also retain the spreading effect brought about by the incorporation of the anionic surfactant.

We claim:

1. A herbicide composition comprising the following components (a), (b) and (c):

(a) paraquat and/or diquat;

(b) an anionic surfactant; and (c) a chelating agent, wherein a molar ratio (c)/(a) of the component (c) to the component (a) is 0.1–3.

2. The composition according to claim 1, wherein the component (a) is contained in a proportion of 0.1–50 wt. %, and a weight ratio (b)/(a) of the component (b) to the component (a) to be incorporated is 0.1–20.

3. The composition according to claim 1, wherein the component (b) is one or more selected from the group consisting of salts of higher fatty acids, alkyl(or alkenyl) sulfates, polyoxyalkylene alkyl(or alkenyl)ether sulfates, polyoxyalkylene alkyl(or alkenyl)aryl ether sulfates, polyoxyalkylene styrylphenyl ether sulfates, mono- or di-alkyl (or alkenyl)benzenesulfonates, alkyl(or alkenyl) naphthalenesulfonates, condensates of an alkyl(or alkenyl) naphthalenesulfonate with formaldehyde, alkyl(or alkenyl) diphenyl ether sulfonates, alkyl(or alkenyl)sulfonates, alkyl (or alkenyl)sulfosuccinates, mono- or di-alkyl(or alkenyl) phosphates, polyoxyalkylene mono- or di-alkyl(or alkenyl) ether phosphates, polyoxyalkylene mono- or di-phenyl ether phosphates, polyoxyalkylene mono- or di-alkyl(or alkenyl) phenyl ether phosphates, salts of polycarboxylic acids, alkyl (or alkenyl)polyoxyalkylene ether acetates and N-methyl-fatty acid taurides.

4. The composition according to claim 1, wherein the component (b) is one or more selected from the group consisting of alkyl(or alkenyl)sulfates, polyoxyalkylene alkyl(or alkenyl)ether sulfates, polyoxyalkylene alkyl(or alkenyl)aryl ether sulfates, alkyl(or alkenyl) naphthalenesulfonates, mono- or di-alkyl(or alkenyl) benzenesulfonates, polyoxyalkylene mono- or di-alkyl(or alkenyl)ether phosphates, polyoxyalkylene mono- or di-phenyl ether phosphates, polyoxyalkylene mono- or di-alkyl(or alkenyl)phenyl ether phosphates, salts of polycarboxylic acids, salts of saturated or unsaturated higher fatty acids and alkyl(or alkenyl)polyoxyalkylene ether acetates.

5. The composition according to claim 1, wherein the component (b) is one or more selected from the group consisting of alkyl(or alkenyl)sulfates, polyoxyalkylene alkyl(or alkenyl)ether sulfates, alkyl(or alkenyl) polyoxyalkylene ether acetates, polyoxyalkylene mono- or di-alkyl (or alkenyl)ether phosphates, salts of saturated or unsaturated higher fatty acids, alkyl(or alkenyl)benzenesulfonates and alkyl(or alkenyl)naphthalenesulfonates.

6. The composition according to claim 1, wherein the component (b) is one or more selected from the group consisting of $C_{8-24}$-alkylsulfates, polyoxyethylene (EO=1–10) $C_{8-24}$-alkyl ether sulfates, polyoxyethylene (EO=1–10) $C_{8-24}$-alkylphenyl ether sulfates, $C_{8-24}$-alkylbenzenesulfonates, $C_{4-24}$-alkylnaphthalenesulfonates, polyoxyethylene (EO=1–10) mono- or di-$C_{8-24}$-alkyl ether phosphates, salts of saturated or unsaturated $C_{8-24}$-fatty acids and $C_{8-24}$-alkyl(or alkenyl)polyoxyethylene (EO=1–20)ether acetates.

7. The composition according to claim 1, wherein the component (c) is selected from the group consisting of aminopolycarboxylic acid type chelating agents, aromatic or aliphatic carboxylic acid type chelating agents, amino acid type chelating agents, ether polycarboxylic acid type chelating agents, phosphonic acid type chelating agents, hydroxycarboxylic acid type chelating agents, polyelectrolyte type chelating agents (including oligomers) and dimethylglyoxime.

8. The composition according to claim 1, wherein the component (c) is selected from the group consisting of ethylenediaminetetraacetic acid (EDTA), cyclohexanediaminetetraacetic acid (CDTA), nitrilotriacetic acid (NTA), iminodiacetic acid (IDA), N-(2-hydroxyethyl)iminodiacetic acid (HIMDA), diethylenetriaminepentaacetic acid (DTPA), N-(2-hydroxyethyl)ethylenediaminetriacetic acid (EDTA-OH), glycol ether diaminetetraacetic acid (GEDTA), oxalic acid, succinic acid, pyruvic acid, glycine, cysteine, malic acid, citric acid, glycolic acid, heptonic acid, tartaric acid, ether polycarboxylic acids represented by the following formula (1):

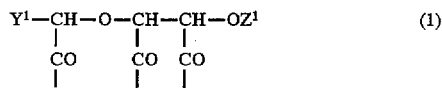

wherein $Y^1$ denotes a hydrogen atom, —$CH_2COOH$ or —COOH, and $Z^1$ means a hydrogen atom,

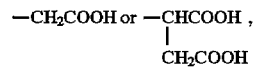

and salts thereof.

9. The composition according to claim 8, wherein the component (c) is selected from the group consisting of ethylenediaminetetraacetic acid, cysteine, glycine, gluconic acid, a compound represented by the formula (1) in which $Y^1$ $CH_2COOH$, and $Z^1$ is H, and salts thereof.

10. A weeding process comprising sprinkling the composition according claim 1 on weeds.

11. The weeding process according to claim 10, wherein a dilute solution in which the concentration of the component (a) is 0.005–8 wt. % is sprinkled on the weeds.

* * * * *

UNITED STATES PATENT AND TRADEMARK OFFICE
CERTIFICATE OF CORRECTION

PATENT NO.  : 5,668,086
DATED       : September 16, 1997
INVENTOR(S) : Tadayuki SUZUKI et al.

It is certified that error appears in the above-indentified patent and that said Letters Patent is hereby corrected as shown below:

On the title page, Item [86], the PCT number should read:

-- PCT/JP94/01953 --

On the title page, Item [75], the Inventors' names should read:

-- Tadayuki Suzuki; Keiko Hasebe; Kazuhiko Kurita
   Yuichi Hioka --

Signed and Sealed this

Second Day of December, 1997

Attest:

BRUCE LEHMAN

*Attesting Officer*  *Commissioner of Patents and Trademarks*